United States Patent
Banks et al.

(10) Patent No.: US 10,444,191 B2
(45) Date of Patent: Oct. 15, 2019

(54) PIPE PIG FOR INSPECTING A PIPELINE

(71) Applicant: 121 PIPELINES LIMITED, Greater Manchester (GB)

(72) Inventors: Steve Banks, Greater Manchester (GB); Sung Quek, Greater Manchester (GB); Vladimir Torres, Greater Manchester (GB); Bosco Fernandes, Greater Manchester (GB)

(73) Assignee: I2I PIPELINES LIMITED, Greater Manchester (GB)

( * ) Notice: Subject to any disclaimer, the term of this patent is extended or adjusted under 35 U.S.C. 154(b) by 47 days.

(21) Appl. No.: 15/575,471

(22) PCT Filed: May 16, 2016

(86) PCT No.: PCT/GB2016/051409
§ 371 (c)(1),
(2) Date: Nov. 20, 2017

(87) PCT Pub. No.: WO2016/185193
PCT Pub. Date: Nov. 24, 2016

(65) Prior Publication Data
US 2018/0172638 A1     Jun. 21, 2018

(30) Foreign Application Priority Data

May 19, 2015 (GB) .................................. 1508570.7

(51) Int. Cl.
*G01N 27/90*     (2006.01)
*F16L 55/38*     (2006.01)
(Continued)

(52) U.S. Cl.
CPC ............ *G01N 27/904* (2013.01); *F16L 55/38* (2013.01); *F16L 55/40* (2013.01); *G01N 27/902* (2013.01); *F16L 2101/30* (2013.01)

(58) Field of Classification Search
CPC ..... G01N 27/904; G01N 27/902; F16L 55/38; F16L 55/40; F16L 2101/30
(Continued)

(56) References Cited

U.S. PATENT DOCUMENTS

| | | | | |
|---|---|---|---|---|
| 5,398,560 A | * | 3/1995 | Zollingger | G01N 27/902 324/220 |
| 6,617,972 B2 | * | 9/2003 | Takarada | G08B 21/0484 324/538 |

(Continued)

FOREIGN PATENT DOCUMENTS

GB         2475736 A         6/2011

OTHER PUBLICATIONS

The International Bureau of WIPO, International Preliminary Report on Patentability and the Written Opinion of the International Searching Authority issued in PCT/GB2016/051409, dated Nov. 21, 2017, 7 Pages.

*Primary Examiner* — Giovanni Astacio-Oquendo
(74) *Attorney, Agent, or Firm* — Taft Stettinius & Hollister LLP; Stephen F. Rost

(57) ABSTRACT

A pipe pig for travelling along the bore of a pipe, the pipe pig comprising a body formed of a deformable material comprising foam, and a plurality of electromagnetic sensors disposed about an outer surface of the body or within the body. The plurality of electromagnetic sensors include means for inducing an electric current in a wall of the pipe, and means for receiving an electromagnetic signal from the wall of the pipe, such that data about the pipe wall can be obtained as the pipe pig travels along a bore of the pipe.

17 Claims, 1 Drawing Sheet

(51) Int. Cl.
*F16L 55/40* (2006.01)
*F16L 101/30* (2006.01)

(58) Field of Classification Search
USPC ........ 324/242, 244, 243, 240, 239, 228, 200
See application file for complete search history.

(56) References Cited

U.S. PATENT DOCUMENTS

| | | | | |
|---|---|---|---|---|
| 7,138,897 | B2 * | 11/2006 | Minerbo | G01V 3/28 |
| | | | | 336/90 |
| 7,265,649 | B1 * | 9/2007 | Hall | E21B 47/01 |
| | | | | 336/84 M |
| 7,419,002 | B2 * | 9/2008 | Dybevik | E21B 43/12 |
| | | | | 166/169 |
| 8,072,221 | B2 * | 12/2011 | Snyder, Jr. | G01V 3/28 |
| | | | | 324/333 |
| 8,779,729 | B2 * | 7/2014 | Shiraishi | G06F 1/3212 |
| | | | | 320/155 |
| 2010/0060273 | A1 | 3/2010 | Couchman | |
| 2012/0291569 | A1 * | 11/2012 | Hill | F16L 55/40 |
| | | | | 73/865.8 |
| 2014/0347055 | A1 * | 11/2014 | Schmidt | G01V 3/12 |
| | | | | 324/338 |

* cited by examiner

PIPE PIG FOR INSPECTING A PIPELINE

This application is a U.S. national stage application under 35 U.S.C. § 371 of PCT International Application Serial No. PCT/GB2016/051409, which has an international filing date of May 16, 2016, designates the United States of America, and claims the benefit of GB Application No. 1508570.7, which was filed on May 19, 2015, the disclosures of which are hereby expressly incorporated by reference in their entirety.

The present invention relates to a pipe pig, and in particular, to a pipe pig for inspecting a pipeline.

BACKGROUND

A pipe pig is a vessel that travels along the bore of a pipeline, such as an oil pipeline. Pipe pigs are often propelled along the pipeline by fluid (e.g. oil) flowing within the pipeline. So-called inspection pipe pigs often include sensors for collecting data about the pipeline as the pipe pig travels along the pipe and may be used to inspect the condition of the pipe walls.

An example of a typical inspection pig is described in US-A-2007022830 which makes use of magnetic flux sensors for collecting data. The sensors are mounted on moveable arms that extend from a rigid body, where the moveable arms ride against the internal profile of the pipeline as the inspection pig travels through the pipe.

Inspection pigs are often long, heavy and expensive pieces of apparatus that require a specialist launching station for inserting the pig into the pipeline and a specialist receiving station for retrieving the pig from the pipeline. As such, the preparation, travel and retrieval of an inspection pipe pig through a pipeline is an expensive, time-consuming and disruptive process. Furthermore, inspection pigs are known for being liable to get stuck within a pipeline and this often results in the pipeline being shutdown until the stuck inspection pig is removed. For certain pipelines (e.g. oil pipelines), any shutdown can be significantly costly. Inspection pigs are often sized for a specific diameter pipeline and have limited ability in negotiating bends in the pipeline or moving between areas of the pipeline with differing diameters. Therefore, a given inspection pig may only be used with pipelines having a suitable specification and multiple inspection pigs are required for inspection of wider ranges of pipelines.

It is an object of certain embodiments of the present invention to provide an improved pipe pig that overcomes at least some of the disadvantages associated with the prior art.

BRIEF SUMMARY OF THE DISCLOSURE

In accordance with an aspect of the present invention there is provided a pipe pig for travelling along the bore of a pipe, the pipe pig comprising:

a body formed of a deformable material comprising foam; and a plurality of electromagnetic sensors disposed about an outer surface of the body or within the body;

wherein the plurality of electromagnetic sensors include means for inducing an electric current in a wall of the pipe, and means for receiving an electromagnetic signal from the wall of the pipe, such that data about the pipe wall can be obtained as the pipe pig travels along a bore of the pipe.

The means for inducing an electric current in the wall of the pipe may include a generating coil for producing a magnetic field.

The generating coil may produce a time varying magnetic field.

In certain embodiments, the means for inducing an electric current in the wall of the pipe may include a magnet, which may be a permanent magnet.

The means for receiving an electromagnetic signal from the wall of the pipe may include a receiving sensor.

The plurality of electromagnetic sensors may be disposed on one or more carriers that are disposed about the outer surface of the body. The outer surface of the body may include one or more recesses for receiving the one or more carriers. Multiple carriers may be provided where each carrier may be arranged on the outer surface of the body along a direction parallel to a longitudinal axis of the body, and wherein each carrier is circumferentially spaced from adjacent carriers. Alternatively, multiple carriers may be provided where each carrier may be arranged on the outer surface of the body along a direction that extends both axially and circumferentially relative to a longitudinal axis of the body.

The body may include an internal cavity for containing one or more electronic components. In certain embodiments, the internal cavity may contain a housing for containing the one or more electronic components. The housing may be removable from the body. In certain embodiments, the housing may comprise a steel or stainless steel housing. In certain embodiments, the housing may be capable of withstanding pressures up to 100 bar, 150 bar, 200 bar, 250 bar or 300 bar.

The one or more electronic components may include an electrical power source for supplying electrical power to the plurality of electromagnetic sensors. The electrical power source may be a rechargeable electrical power source.

Additionally or alternatively, the one or more electronic components may include a memory for receiving data from the plurality of electromagnetic sensors.

The pipe pig may further comprise a coating covering the plurality of electromagnetic sensors. The coating may provide a protective layer that may reduce the wear of the body or electromagnetic sensors and may comprise a polymeric material, such as polyurethane.

The foam may be an open cell foam such as polyurethane foam. The density of the foam may vary depending on the specific requirements (e.g. deformability) of the pipe pig.

In accordance with another aspect of the present invention, there is provided an apparatus for attachment to a pipe pig, the apparatus comprising a carrier and a plurality of electromagnetic sensors supported on the carrier;

wherein the carrier is configured to be mounted on an outer surface of a body of a pipe pig; and the plurality of electromagnetic sensors include means for inducing an electric current in a wall of the pipe, and means for receiving an electromagnetic signal from the wall of the pipe, such that data about the pipe wall can be obtained as the pipe pig travels along a bore of the pipe.

The means for inducing an electric current in the wall of the pipe may include a generating coil for producing a magnetic field. The generating coil may produce a time varying magnetic field.

The means for inducing an electric current in the wall of the pipe may include a magnet, where the magnet may be a permanent magnet.

The means for receiving an electromagnetic signal from the wall of the pipe may include a receiving sensor.

BRIEF DESCRIPTION OF THE DRAWINGS

Embodiments of the invention are further described hereinafter with reference to the accompanying drawings, in which.

DETAILED DESCRIPTION

Figure 1:
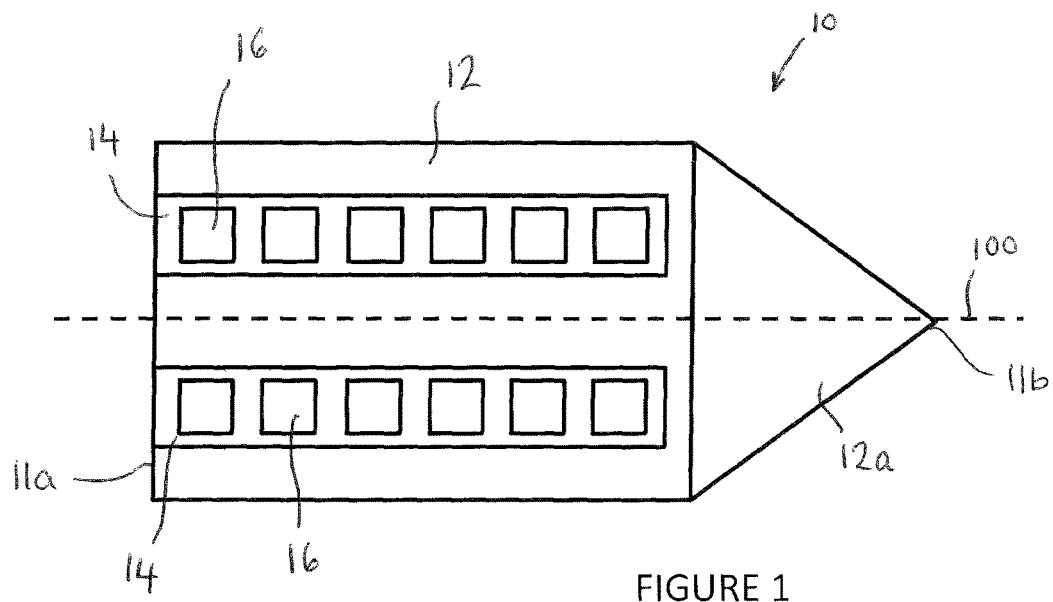
FIG. 1 is a schematic view of a pipe pig in accordance with an embodiment of the present invention.

A pipe pig 10 in accordance with an embodiment of the present invention is shown schematically in FIG. 1. The pipe pig 10 extends generally along a longitudinal axis 100 from a rear end 11a to a front end 11b. Throughout the present specification, directions that are parallel to the longitudinal axis 100 are referred to as axial, directions radiating from the longitudinal axis 100 are referred to as radial, and directions around the longitudinal axis 100 are referred to as circumferential. The pipe pig 10 has a body 12 made of a deformable material and is generally cylindrical with a tapered front section 12a. In certain embodiments, the tapered front section 12a may be conical, as shown in the Figures. In other embodiments, the tapered front section 12a may be frustoconical or otherwise tapered. The pipe pig 10 is intended to travel along the bore of a pipe line in the forward (i.e. towards the front end 11b) direction. A tapered front section 12a may therefore facilitate passage of the pipe pig 10 in the bore in the event that any obstacles are present. In certain embodiments, the tapered front section 12a may include an attachment (not shown) such as a bar or loop that may facilitate the attachment of a tether. The tether may be used to pull the pipe pig 10 along the pipe bore (although, generally, the pipe pig 10 may be caused to move along the pipe bore due to the fluid pressure of the flowing fluid within the pipe), or to retrieve the pipe pig 10 from the pipe after use.

In certain embodiments, the deformable material forming the body 12 may be foam. For example, the foam may be an open cell foam such as polyurethane foam. The density of the deformable material may vary depending on the specific requirements (e.g. deformability) of the pipe pig 10.

The pipe pig 10 includes a plurality of electromagnetic sensors 16 disposed about an outer surface of the body 12. In the non-limiting embodiment shown in FIG. 1, the electromagnetic sensors 16 are disposed in groups on carriers 14 which support the electromagnetic sensors 16 and extend axially along the outer surface of the body 12. In alternative embodiments, the electromagnetic sensors 16 may not be supported on a carrier 14 and may be supported directly on the body 12. Whether with or without a carrier 14, the electromagnetic sensors 16 may be arranged on the body 12 in a helical arrangement relative to the longitudinal axis 100. In this sense, a helical arrangement is one that extends both axially and circumferentially about the longitudinal axis 100. In certain embodiments, the electromagnetic sensors 16 may be disposed within (e.g. embedded within) the material of body 12. In any embodiment, it is preferable for the electromagnetic sensors 16 to be arranged such that radial compression of the body 12 does not result in electromagnetic sensors 16 contacting one another. Such contact could lead to damage and limit the deformability of the pipe pig 10 and therefore reduce the maneuverability of the pipe pig 10 in a pipe.

In certain embodiments, the outer surface of the body 12 may include one or more recesses for receiving the plurality of sensors 16. In particular, the recesses may receive the carriers 14. In any embodiment where recesses are present, the recesses may serve to support the plurality of sensors 16 at a radial position that is radially inward relative to the remainder of the outer surface of the body 12. Such an arrangement may limit or prevent damage to the plurality of sensors 16 during travel of the pipe pig 10 along the pipe bore. In further or alternative embodiments, the pipe pig 10 may include a coating that covers some or the entire outer surface of the body 12, where the coating may cover some or all of the plurality of sensors 16. The coating may comprise a polymeric material such as polyurethane, for example. The coating may be applied in any suitable manner including but not limited to painting, spraying, moulding, and adhering a formed layer to the body 12.

The electromagnetic sensors 16 include means for inducing an electric current in a wall of a pipe as the pipe pig 10 travels through the bore of the pipe. In certain embodiments, the means for inducing an electric current in the pipe wall may include a generating coil that is energized to produce a magnetic field which, in turn, induces an electric current in the pipe wall. The magnetic field produced by the generating coil may be a time varying magnetic field (e.g. by energizing the generating coil with an AC current). Alternatively, the magnetic field may not be time varying and the movement of the generating coil (which is attached to the moveable pipe pig 10) relative to the pipe wall may cause the induction of an electric current in the pipe wall. In further alternative embodiments, the means for inducing an electric current in the pipe wall may include a magnet (e.g. a permanent magnet or electro-magnet) that moves (by virtue of the moving pipe pig 10) relative to the pipe wall to induce an electric current therein.

The electromagnetic sensors 16 additionally include means for receiving an electromagnetic signal from the wall of the pipe, such that data about the pipe wall can be obtained as the pipe pig 10 travels along the bore of the pipe. In certain embodiments, the means for receiving an electromagnetic signal from the wall of the pipe include a receiving sensor. For example, the receiving sensor may be a coil wherein a current is induced in the coil in response to an electromagnetic signal. In certain embodiments, the electromagnetic sensors 16 may be any sensors capable of performing eddy current testing.

The electromagnetic sensors 16 may be provided as one or more printed circuit boards (PCBs) which may, in certain embodiments, be flexible. In certain embodiments, each sensor may include a single generating coil and two receiving sensors.

Figure 2:
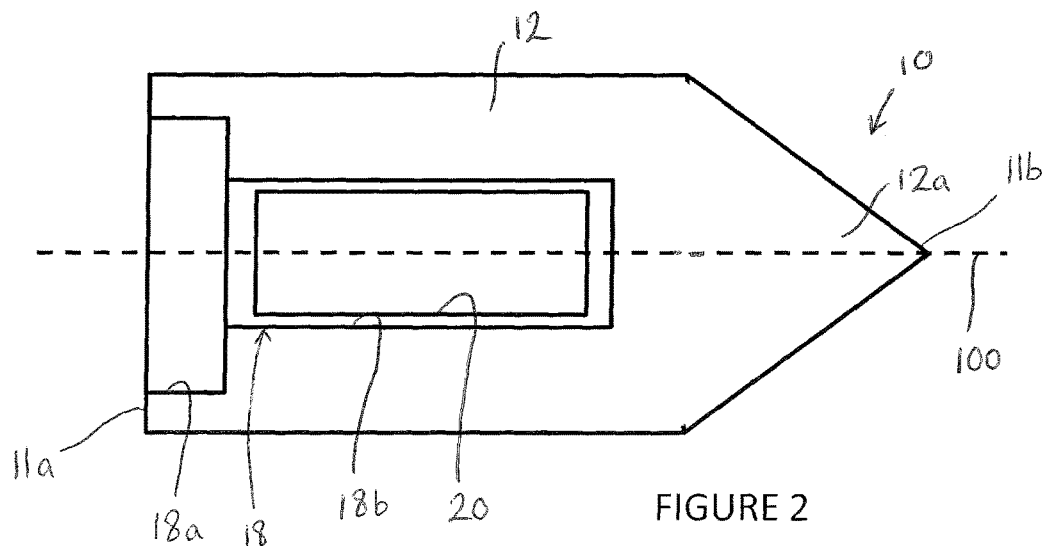
FIG. 2 is a schematic cross sectional view of the pipe pig of FIG. 1.

In the cross-sectional view shown in FIG. 2, the body 12 can be seen to include an internal cavity 18. In the non-limiting embodiment shown in FIG. 2, the internal cavity 18 has a rear part 18a and a forward part 18b where the rear part 18a has a greater diameter relative to the forward part 18b. In use, the internal cavity 18 may contain one or more electronic components selected from but not limited to an electrical power source (which may be rechargeable) for supplying electrical power to the plurality of electromagnetic sensors 16, a memory for receiving data from the plurality of electromagnetic sensors 16, and a processor for processing data received from the plurality of electromagnetic sensors 16. The one or more electronic components may be housed within the cavity 18 in a housing 20 that serves to provide protection to the electronic components. The housing 20 may be pressure resistant so that the housing 20 maintains its integrity and continues to protect the electronic components in a pressurized environment within the pipe. In certain embodiments, the housing 20 may be capable of withstanding (e.g. remaining fluid tight) pressures up to 100 bar, 150 bar, 200 bar, 250 bar or 300 bar. The housing 20 is preferably made of a suitable material, and may, for example, comprise steel or stainless steel. The housing 20 may be removable from the body 12 such that the electronic components can be retrieved, interrogated (e.g. access and/or remove data from the memory), or replaced (e.g. if damaged) between uses of the pipe pig 10 in a pipe. The housing 20 may be reusable such that it can be interchanged between pipe pigs 10. This may be particularly useful if the pipe pig 10 has become damaged or worn and requires replacement, and allows the more costly components (contained within the housing 20) to be retrieved and reused.

The electronic components may be electrically connected to the plurality of sensors 16 via one or more electrical connectors. In certain embodiments, the housing 20 may include an electrical connection through which electrical connections between the plurality of sensors 16 and the electronic components may be made. The rear part 18a of the cavity 18 may serve to protect some or all of the electrical connectors from damage as the pipe pig 10 travels within a pipe bore.

In one example, the pipe pig 10 may be formed by moulding the body 12 and then attaching the plurality of sensors 16. Whilst in the above-described embodiments the plurality of sensors 16 are disposed about an outer surface of the body 12, in alternative embodiments, the plurality of sensors 16 may be disposed within the body 12. For example, the plurality of sensors 16 may be embedded within the body 12 by moulding the body 12 around the plurality of sensors 16.

In one aspect of the invention, the plurality of sensors 16 may be supported on a carrier 14 that is provided for attachment to a pipe pig 10 in a desired arrangement.

In use, the pipe pig 10 is inserted into the bore of a pipe and travels along the pipe bore. As noted above, the pressure of the fluid within the pipe (e.g. oil) may serve to propel the pipe pig 10 along the pipe. For the pipe pig 10 to be propelled by the fluid within the pipe, the pipe pig 10 (or at least a part of it) preferably has a diameter that is comparable to the internal diameter of the pipe. In other, less preferable embodiments, the pipe pig 10 may be propelled by other means, e.g. pulled along the pipe by a tether. During travel, the plurality of sensors 16 induce electric currents in the wall of the pipe. The induced electric currents may be eddy currents, for example. The induced electric currents are then monitored by receiving electromagnetic signals from the wall of the pipe using the electromagnetic sensors 16. Variations in the electric currents (e.g. the phase and/or magnitude) may indicate the presence of flaws, defects, or irregularities in the pipe wall. The pipe pig 10 may therefore serve as an effective inspection tool that may provide an overview of the pipeline condition over the travel path. Areas of corrosion and cracking within the pipeline can therefore be identified. Additionally, since the body 12 of the pipe pig 10 is formed of a deformable material, the pipe pig 10 also has the benefits of a traditional utility pig, where it does not present a significant risk of becoming stuck in the pipe, and it may perform other operations such as the cleaning or drying of the pipeline. For example, pipe pigs 10 in accordance with embodiments of the present invention may be capable of compressing to a diameter around 50% of an uncompressed state. The deformability of the body 12 may allow the pipe pig 10 to negotiate multi-diameter pipelines (e.g. variations between 18 inch (~46 cm) and 24 inch (~61 cm)). Furthermore, the body 12 may be formed of relatively inexpensive materials making the pipe pig 10 more economically attractive for frequent and widespread use. Additionally, specialist launching and retrieving stations are not necessary for inserting and retrieving pipe pigs 10 accordingly to certain embodiments of the present invention thereby reducing the time, cost and logistical effort associated with using the pipe pigs 10 in contrast with prior art inspection pigs.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A pipe pig for travelling along the bore of a pipe, the pipe pig comprising:
    a body formed of a deformable material comprising foam; and
    a plurality of electromagnetic sensors disposed about an outer surface of the body or within the body;
    wherein the plurality of electromagnetic sensors include means for inducing an electric current in a wall of the pipe, and means for receiving an electromagnetic signal from the wall of the pipe, such that data about the pipe wall can be obtained as the pipe pig travels along a bore of the pipe,
    wherein the body includes an internal cavity for containing one or more electronic components, the internal cavity contains a housing for containing the one or more electronic components and the housing is capable of withstanding pressures up to 100 bar, 150 bar, 200 bar, 250 bar or 300 bar.

2. The pipe pig of claim 1, wherein the means for inducing an electric current in the wall of the pipe include a generating coil for producing a magnetic field.

3. The pipe pig of claim 2, wherein the generating coil produces a time varying magnetic field.

4. The pipe pig of claim 1, wherein the means for inducing an electric current in the wall of the pipe include a magnet.

5. The pipe pig of claim 4, wherein the magnet is a permanent magnet.

6. The pipe pig of claim 1, wherein the means for receiving an electromagnetic signal from the wall of the pipe include a receiving sensor.

7. The pipe pig of claim 1, wherein the plurality of electromagnetic sensors are disposed on one or more carriers that are disposed about the outer surface of the body.

8. The pipe pig of claim 7, wherein the outer surface of the body includes one or more recesses for receiving the one or more carriers.

9. The pipe pig of claim 7, wherein multiple carriers are provided and each carrier is arranged on the outer surface of the body along a direction parallel to a longitudinal axis of the body, and wherein each carrier is circumferentially spaced from adjacent carriers.

10. The pipe pig of claim 7, wherein multiple carriers are provided and each carrier is arranged on the outer surface of the body along a direction that extends both axially and circumferentially relative to a longitudinal axis of the body.

11. The pipe pig of claim 1, wherein the housing is removable from the body.

12. The pipe pig of claim 1, wherein the housing comprises a steel or stainless steel housing.

13. The pipe pig of claim 1, wherein the one or more electronic components includes an electrical power source for supplying electrical power to the plurality of electromagnetic sensors.

14. The pipe pig of claim 13, wherein the electrical power source is a rechargeable electrical power source.

15. The pipe pig of claim 1, wherein the one or more electronic components includes a memory for receiving data from the plurality of electromagnetic sensors.

16. The pipe pig of claim 1, further comprising a coating covering the plurality of electromagnetic sensors.

17. The pipe pig of claim 16, wherein the coating comprises a polymeric material.

* * * * *